United States Patent [19]

Vanstone et al.

[11] E Patent Number: Re. 33,109

[45] Reissued Date of Patent: Nov. 7, 1989

[54] CHALCONE DERIVATIVES

[75] Inventors: Anthony E. Vanstone, Whitton; Graham K. Maile; Lynn K. Nalbantoglu, both of London, all of England

[73] Assignee: Biorex Laboratories Limited, London, England

[21] Appl. No.: 179,223

[22] Filed: Apr. 8, 1988

Related U.S. Patent Documents

Reissue of:

[64] Patent No.: 4,656,305
Issued: Apr. 7, 1987
Appl. No.: 789,277
Filed: Oct. 18, 1985

[30] Foreign Application Priority Data

Oct. 19, 1984 [GB] United Kingdom ..... 84-26424

[51] Int. Cl.[4] ..... C07C 69/76

[52] U.S. Cl. ..... 560/54; 560/51; 514/533; 549/230; 562/464

[58] Field of Search ..... 560/51, 54; 514/533; 549/230; 260/507 R; 562/464

[56] References Cited

FOREIGN PATENT DOCUMENTS 125736 11/1976 Japan .
1566497 4/1980 United Kingdom ..... 560/54

OTHER PUBLICATIONS

Baker, S. et al., J. Chem. Soc. Perkins Trans 1(1), 178-81, 1981.
Aust. J. Chem. 32(7), 1601-12, 1979.
Kolsaker, P. et al., Tetrahedron 29(8), 1095-100, 1973.
Gaurmelon, C. et al., Bull. Soc. Chim. Fr. (7-8,PE 2) 1639-45, 1975.
Gupta, A. et al., Indian J. Chem. Soc. Sec. B 14(B)11, 903-4, 1976.
Kyogokun et al. CA 91:20115y.

*Primary Examiner*—Paul J. Killos
*Attorney, Agent, or Firm*—Wenderoth, Lind & Ponack

[57] ABSTRACT

The present invention provides chalcone derivatives of the general formulae:

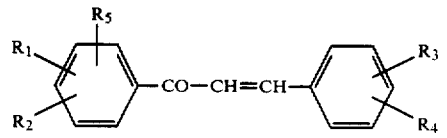

(IIa)

and

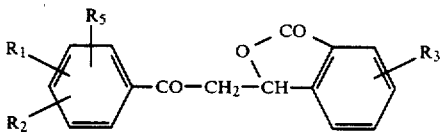

(IIb)

wherein $R_1$ is a hydroxyl, carboxylic or sulphonic acid group or a carboxyalkoxy or sulphoalkoxy radical, $R_2$ is an unsaturated, straight-chained or branched aliphatic hydroxycarbonyloxy radical, $R_3$ is a hydrogen atom, a hydroxyl group or an alkoxy radical, $R_4$ is an alkyl, hydroxyalkyl, alkoxy, carboxyalkoxy, sulphoalkoxy or carboxyalkylcarbonyloxyalkyl radical or a carboxylic acid or sulphonic acid group and $R_5$ is a hydrogen or halogen atom, with the proviso that compounds of general formula (IIa) always contain at least one carboxylic or sulphonic acid group; and the nontoxic inorganic and organic salts of those compounds containing at least one carboxylic acid or sulphonic acid group.

The present invention also provides a process for the preparation of these chalcone derivatives, as well as pharmaceutical compositions containing them.

12 Claims, No Drawings

CHALCONE DERIVATIVES

Matter enclosed in heavy brackets [ ] appears in the original patent but forms no part of this reissue specification; matter printed in italics indicates the additions made by reissue.

The present invention is concerned with new and pharmaceutically useful chalcone derivatives and with the preparation thereof.

In our earlier British Patent Specification No. 1,566,497, there are described and claimed chalcone derivatives of the general formulae:

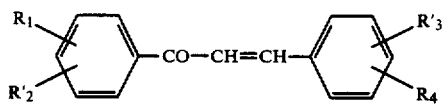

(Ia)

and

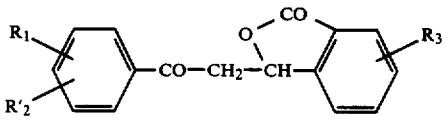

(ib)

wherein $R_1$ is a hydroxyl, carboxylic acid or sulphonic acid group or a carboxyalkoxy or sulphoalkoxy radical, $R'_2$ and $R'_3$, which may be the same or different, are hydrogen or halogen atoms, hydroxyl groups or alkoxy radical and $R_4$ is an alkyl, hydroxyalkyl, alkoxy, carboxyalkoxy, sulphoalkoxy or carboxyalkylcarbonyloxyalkyl radical or a carboxylic acid or sulphonic acid group, with the proviso that compounds of general formula (Ia) always contain at least one carboxylic acid or sulphonic acid group; and the non-toxic inorganic and organic salts of those compounds containing at least one carboxylic acid or sulphonic acid group.

Furthermore, British Patent Specification No. 1,523,241 describes and claims chalcone derivatives of the general formula:

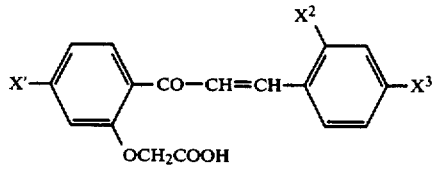

wherein one or two of $X^1$, $X^2$ and $X^3$ is/are 3-methyl-2-butenyloxy (=isoprenyloxy) and the other is/are hydrogen. These compounds are said to have anti-gastric and anti-duodenal ulcer activities, the most active compound being said to be 2'-carboxymethoxy-4,4'-bis-(3-methyl-2-butenyloxy)-chalcone (=1-(4-isoprenyloxy-2-carboxymethoxyphenyl)-3-(4-isoprenyloxyphenyl)-prop-2-en-1-one).

In further development of our earlier invention, we have now found that compounds of the above-given general formulae (Ia) and (Ib), in which $R'_2$ is an unsaturated, straight-chained or branched aliphatic hydrocarbonyloxy radical, have a greatly improved pharmaceutical activity, for example for treating inflammatory and allergic conditions and for treating ulcerous conditions of the gastro-intestinal tract, as well as a good analgesic activity.

Thus, the new chalcone derivatives according to the present invention are compounds of the general formulae:

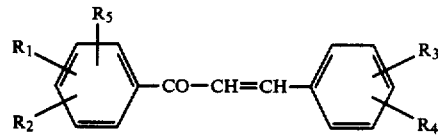

(IIa)

and

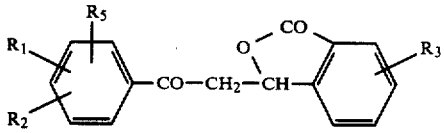

(IIb)

wherein $R_1$ is a hydroxyl, carboxylic acid or sulphonic acid group or a carboxyalkoxy or sulphoalkoxy radical, $R_2$ is an unsaturated, straight-chained or branched aliphatic hydrocarbonyloxy radical, $R_3$ is a hydrogen atom, a hydroxyl group or an alkoxy radical, $R_4$ is an alkyl, hydroxyalkyl, alkoxy, carboxyalkoxy, sulphoalkoxy or carboxyalkylcarbonyloxyalkyl radical or a carboxylic acid or sulphonic acid group and $R_5$ is a hydrogen or halogen atom, with the proviso that compounds of general formula (IIa) always contain at least one carboxylic acid or sulphonic acid group; and the non-toxic inorganic and organic salts of those compounds containing at least one carboxylic acid or sulphonic acid group.

It is to be expected that the ethylenic double bond of the new chalcone derivatives (IIa) is in the more thermodynamically stable trans form.

Carboxyalkoxy and sulphoxyalkoxy radicals $R_1$ and $R_4$ are preferably of the general formulae $$—O(CH_2)_nCOOH \text{ or } —O—(CH_2)_nSO_3H$$

in which n is an integer equal to or greater than 1 and is preferably 1 to 3. In the case of $R_1$, this is especially preferably a carboxymethoxy radical.

When $R_5$ is a halogen atom, it can be a chlorine fluorine, bromine or iodine atom.

The substituent $R_2$ preferably contains up to 6 carbon atoms and can contain one or more double and/or triple bonds, the isoprenyloxy, prop-2-enyloxy and propargyloxy radicals being especially preferred.

The alkyl, hydroxyalkyl and alkoxy radical constituting or forming part of substituents in the new compounds according to the present invention preferably contain up to 6 carbon atoms and more preferably contain up to 3 carbon atoms.

The new compounds according to the present invention can be prepared, for example, by condensing an acetophenone derivative of the general formula:

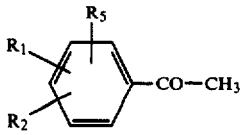

(III)

in which $R_1$, $R_2$ and $R_5$ have the same meanings as above, with an aldehyde of the general formula:

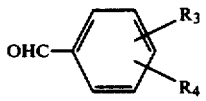

(IV)

in which $R_3$ and $R_4$ have the same meanings as above.

This condensation reaction is preferably carried out in the presence of a strong base, for example an alkali metal hydroxide, in an aqueous or aqueous organic medium.

The reaction can be carried out at a temperature between ambient temperature and the boiling point of the reactive mixture.

When a product is obtained in which $R_4$ is a hydroxyalkyl radical, this can, if desired, be subsequently reacted with an appropriate reactive derivative of an alkane-dicarboxylic acid to give the corresponding carboxyalkylcarbonyloxyalkyl compound.

When $R_4$ is a carboxyl group in the o-position, the product can, if desired, be subsequently lactonised to give a compound of general formula (IIb).

Since the product obtained contains at least one free carboxylic or sulphonic acid group, this can, if desired, be subsequently reacted with a non-toxic inorganic or organic base to give the corresponding salt. Preferred inorganic bases include basic compounds of the alkali and alkaline earth metals, such as sodium, potassium and calcium hydroxide and carbonate and preferred organic bases include mono, di- and trialkylamines.

The present invention also provides pharmaceutical compositions containing at least one of the new compounds, in admixture with a solid or liquid pharmaceutical diluent or carrier.

Pharmacological tests have been carried out in order to demonstrate the advantageous properties possessed by the new compounds according to the present invention, in comparison with two known compounds with chemically similar structures. The following compounds were used:

Compound A: 1-(4-isoprenyloxy-2-carboxymethoxyphenyl)-3-(4-isoprenyloxyphenyl)-prop-2-en-1-one (according to British Patent No. 1523241).

Compound B: 1-(4-carboxymethoxyphenyl)-3-(4-carboxyphenyl)-prop-2-en-1-one (according to British Patent No. 1566497)

Compound C: 1-(4-isoprenyloxy-2-carboxymethoxyphenyl)-3-(4-carboxyphenyl)-prop-2-en-1-one (according to the present invention; Example 1)

Compound D: 1-(2-carboxymethoxy-4-isoprenyloxyphenyl)-3-(4-carboxymethoxyphenyl)-prop-2-en-1-one (according to the present invention; Example 2)

Compound E: 1-(2-carboxymethoxy-4-isoprenyloxyphenyl)-3-(4-carboxymethoxy-3-methoxyphenyl)-prop-2-en-1-one (according to the present invention; Example 3)

Compound F 1-(4-isoprenyloxy-2-carboxymethoxyphenyl)-3-(3-carboxyphenyl)-prop-2-en-1-one (according to the present invention: Example 4).

A. Anti-ulcer Activity

Method Ethanol-induced gastric necrosis in rats; modification of A. Robert et al., Gastroenterol., 77, 433–443/1979.

| compound | oral dose mg./kg. | erosion length (mm.) mean and range | inhibition compared with control (%) | $\sqrt{\text{erosion length (mm.)}}$ mean and range | inhibition compared with control (%) |
|---|---|---|---|---|---|
| Control (starch mucilage) | — | 106 (29–175) | — | 10.0 (5.4–13.2) | — |
| A | 70 | 68 (3–167) | 36 | 7.6 (1.7–12.9) | 24 |
| A* | 280 | 54 (5–122) | 49 | 6.7 (2.1–11.0) | 33 |
| C | 70 | 27 (6–112) | 75 | 4.8 (2.4–10.6) | 52 |
| D* | 70 | 21 (6–37) | 80 | 4.3 (2.3–6.0) | 57 |
| E* | 70 | 45 (10–75) | 58 | 6.8 (3.1–8.7) | 32 |
| F* | 70 | 31 (7–112) | 71 | 5.0 (2.6–10.6) | 50 |

Results of two separate experiments. Number of animals (n): *n=8, otherwise n=16. Vehicle or test compounds administered 15 minutes prior to oral administration of 1 ml. ethanol/rat. All rats sacrificed 1 hour after ethanol administration.

Anti-ulcer activity

Method: Ethanol-induced gastric lesions in rats, B. Y. C. Wan and S. Gottfried, J. Pharm. Pharmacol., 37/1985 (in the press).

| compound | oral dose (mg./kg.) | inhibition % |
|---|---|---|
| A | 70 | 50 |
| B | 70 | 71 |
| C | 70 | 88 |

B. Anti-inflammatory activity: dextran oedema in rats

| compound | oral dose (mg./kg.) | inhibition % |
|---|---|---|
| B | 200 | 21 |
| C | 200 | 47 |

C. Anti-inflammatory activity: sodium urate oedema in rats

| compound | oral dose (mg./kg.) | inhibition % |
|---|---|---|
| B | 100 | 45 |
| C | 100 | 58 |

D. Analgesic activity: acetic acid writhing in mice

| compound | oral dose (mg./kg.) | inhibition % |
|---|---|---|
| B | 100 | 48 |
| C | 100 | 64 |

E. Carrageenin hyperalgesia in rats

| compound | oral dose (mg./kg.) | inhibition % |
|---|---|---|
| B | 100 | 64 |
| C | 100 | 103 |

F. Inhibition of rat gastric mucosal 15-OH prostaglandin dehydrogenase

This is a test for potential anti-ulcer activity (see Muramatsu et al., Biochem. Pharmacol., 2629-2633/1984)

| compound | inhibition of enzyme activity % | |
|---|---|---|
| | $10^{-4}$ M | $10^{-3}$ M |
| A | 14 | 44 |
| B | 12 | 54 |
| C | 34 | 84 |

The results of all of the tests given above clearly show the superiority of compound C according to the present invention in comparison with the similar but known compounds A and B.

The following examples are given for the purpose of illustrating the present invention:

EXAMPLE 1

1-(4-Isoprenyloxy-2-carboxymethoxyphenyl)-3-(4-carboxyphenyl-prop-2-en-1one (a) 74 ml. isoprene were mixed with 80 ml. 45% hydrobromic acid in glacial acetic acid, with external ice cooling. The mixture was kept for 48 hours at 4° C. and then poured into ice water. The reaction product was thoroughly extracted with diethyl ether and the ethereal extract was washed with 3% by weight aqueous sodium bicarbonate solution until all the acetic acid had been removed. After drying with anhydrous calcium chloride, the isoprenyl bromide formed was distilled off; b.p 52°-54° C./20 mm.Hg, yield 65.2 g. The boiling point and infra-red spectrum of the product were in agreement with the literature. The NMR spectrum ($CDCl_3$) confirmed the structure.

(b) A mixture of 11 g. potassium carbonate, 10 g. 2,4-dihydroxyacetophenone, 9 ml. isoprenyl bromide and 200 ml. dry acetone was magnetically stirred at ambient temperature for 5 hours, after which time thin layer chromatography indicated that the reaction was complete (TLC solvent system: petroleum ether/-diethyl ether/acetone 8:1:1 v/v/v). The mixture was filtered and the collected potassium carbonate was washed well with acetone. The acetone solution was concentrated to a small volume, diethyl ether was added, the solution was filtered and again concentrated. Petroleum ether (b.p. 40°-60° C.) was added and the mixture left to stand at 4° C. to allow crystallisation. There was obtained a first crop of 8.4 g. of 4-isoprenyloxy-2-hydroxyacetophenone and a second crop of 1.4 g. Thin layer chromatography indicated that both crops had a degree of purity of more than 99%; m.p. 40°-42° C. The NMR spectrum confirmed the expected structure.

(c) A mixture of 10.2 g. 4-isoprenyloxy-2-hydroxyacetophenone, 3.3 g. potassium hydroxide and 100 ml. dry acetone was stirred for 30 minutes at ambient temperature, 5.3 ml. ethyl bromoacetate were added dropwise thereto and the resultant mixture then stirred for 5 hours at ambient temperature. A thin layer chromatogram (petroleum ether (b.p. 60°-80° C.)/diethyl ether-/acetone 8:1:1 v/v/v) indicated that the reaction was complete. The reaction mixture was filtered and the solid filtered off was washed with acetone. Diethyl ether was added to the filtrate, followed by treatment with decolorising charcoal. Removal of most of the solvent, plus the addition of petroleum ether (b.p. 40°-60° C.), gave 8.1 g. of crystalline 4-isoprenyloxy-2-carboethoxymethoxyacetophenone; m.p. 59°-60° C. A thin layer chromatogram indicated that the product had a degree of purity of more than 99%. The NMR spectrum confirmed the structure.

(d) 5.1 g. 4-Isoprenyloxy-2-carboethoxymethoxyacetophenone were dissolved in a solution of 2.2 g. sodium hydroxide in 10 ml. water and 2.5 g. 4-carboxybenzaldehyde were added to the solution. The reaction mixture was then shaken vigorously until the product precipitated. After standing for 10 minutes at ambient temperature, the product was filtered off, rinsed with the mother liquors and then washed three times with industrial methylated spirit. The product was finally washed with diethyl ether and then dried to constant weight in a vacuum oven at 60° C. to give 5.43 g. 1-(4-isoprenyloxy-2-carboxymethoxy-phenyl)-3-(4-carboxyphenyl)-prop-2-en-1-one in the form of its disodium salt. A thin layer chromatogram (ethyl acetate/-methanol/30% aqueous trimethylamine 7:2:4 v/v/v) indicated that the product had a degree of purity of more than 99%. The product had a melting point of >360° C. A 10% aqueous solution of the product had a pH of 7.5.

A sample of the disodium salt was dissolved in water and acidified and the precipitated solid was washed with water until the washings were neutral, whereafter the product was dried to constant weight in a vacuum oven at 60° C. The diacid thus obtained had a melting point of 239°-240° C. The NMR spectrum ($d_6$-DMSO) confirmed the structure.

EXAMPLE 2

1-(2-Carboxymethoxy-4-isoprenyloxyphenyl)-3-(4-carboxymethoxyphenyl)-prop-2-en-1-one 12.24 g. 2-Carboxymethoxy-4-isoprenyloxyacetophenone were dissolved in a solution of 5 g. sodium hydroxide in 24 ml. water in a 50 ml. round-bottom flask and about 2 ml. methanol added thereto. When dissolving was complete, 6.96 g. of finely ground 4-carboxymethoxybenzaldehyde were added and the flask was stopped and shaken vigorously for 10 minutes. Solid commenced to precipitate and the reaction mixture was left to stand for 10 minutes at ambient temperature. The precipitated solid was filtered off, washed well with methanol and the product collected by centrifuging. The product was dried to constant weight in a vacuum oven at 70° C. to give 15.88 g. 1-(2-carboxymethoxy-4-isoprenyloxyphenyl)-3-(4-carboxymethoxyphenyl)-prop-2en-1-one in the form of its disodium salt.

The solid was dissolved in 70 ml. of hot distilled water and filtered. About 400 ml. methanol were added to the filtrate and the resultant solution left to cool in a cold room at 4° C. The precipitated solid was filtered off, washed with a small volume of methanol and then dried to constant weight in a vacuum oven at 70° C., a first crop of 5.57 g. being obtained. Concentration of the mother liquor gave a second crop of 5.11 g. Thin layer chromatography (ethyl acetate/methanol/30% aqueous trimethylamine 7:2:4 v/v/v) indicated that both crops had a degree of purity greater than 99%. The product had a melting point of >360° C. A 10% aqueous solution thereof had a pH of 7.7.

A sample of the disodium salt was converted into the corresponding free diacid by acidification with dilute hydrochloric acid. The diacid was filtered off, washed with water until the washings were neutral and then dried to constant weight in a vacuum oven at 70° C. Then layer chromatography (ethyl acetate/methanol/30% aqueous trimethylamine 7:2:4 v/v/v) indicated that the product had a degree of purity greater than 99%. The diacid had a melting point of 167°-168° C.

EXAMPLE 3

1-(2-Carboxymethoxy-4-isoprenyloxyphenyl)-3-(4-carboxymethoxy-3-methoxyphenyl)-prop-2-en-1-one (a) 30.4 g. 4-Hydroxy-3-methoxybenzaldehyde (vanillin) were added to 300 ml. dry dimethylformamide and the resultant mixture magnetically stirred at ambient temperature. 9.2 g. Sodium hydride (50% oil dispersion) were added over a period of 30 minutes, whereafter the reaction mixture was allowed to come to ambient temperature. 24.6 g. Ethyl chloroacetate in 200 ml. dry dimethylformamide were then added and the reaction mixture was stirred for 3 days at ambient temperature, whereafter thin layer chromatography (petroleum ether/dichloromethane/acetone 6:3:1 v/v/v) indicated that the reaction was 90% complete.

The reaction mixture was dissolved in 900 ml. water and extracted twice with 300 ml. amounts of diethyl ether. The organic layer was washed three times with 200 ml. amounts of distilled water until the washings were neutral and then dried over anhydrous sodium sulphate. The dried extract was filtered and the filtrate evaporated to dryness. The resultant solid was slurried with petroleum ether (b.p. 40°-60° C.), filtered and dried in a vacuum desiccator to give 28.89 g. 4-carboethoxymethoxy-3-methoxybenzaldehyde; m.p. 59°-61° C. Thin layer chromatography (petroleum ether/dichloromethane/acetone 6:3:1 v/v/v) indicated that the product had a degree of purity greater than 99%. The NMR spectrum was in accordance with the expected structure.

(b) A solution of 18 g. 4-carboethoxymethoxy-3-methoxybenzaldehyde in 40 ml. of a 22% aqueous solution of sodium hydroxide containing 4 ml. methanol was mixed with a solution of 40.8 g. 2-carboethoxymethoxy-4-isoprenyloxyacetophenone 40 ml. of a 22% aqueous solution of sodium hydroxide containing 4 ml. methanol. Thorough mixing was continued until precipitation of the product occurred. The reaction mixture was left for a further 15 minutes and the precipitated product was then filtered off and washed with ethanol. The solid was slurried in ethanol and again filtered, this procedure being carried out twice. After removal of most of the ethanol by distillation under reduced pressure, the solid product was dissolved in about 200 ml. hot water, filtered and the filtrate mixed with an equal volume of the methanol. The pH of the resultant solution was adjusted to 8.5 by the careful addition of dilute acetic acid and the product then precipitated using an excess of ethanol. The precipitated product was filtered off, washed well with ethanol and dried in a vacuum oven at 40° C. There were obtained 27.0 g 1-(2-carboxymethoxy-4-isoproprenyloxyphenyl)-3-(4-carboxymethoxy-3-methoxyphenyl)-prop-2-en-1-one in the form of the disodium salt; m.p. >200° C. Thin layer chromatography (ethyl acetate/methanol/30% aqueous trimethylamine 7:2:4 v/v/v) indicated that the product had a degree of purity greater than 99%.

A sample of the disodium salt was acidified to give the free diacid; m.p. 144°-150° C. The NMR spectrum supported the expected structure of the diacid and hence of the corresponding disodium salt.

EXAMPLE 4

1-(4-Isoprenyloxy-2-carboxymethoxyphenyl)-3-(3-carboxyphenyl)-prop-2-en-1-one 20.4 g. Isoprenyloxy-2-carboxymethoxyacetophenone and 11.0 g. 3-carbomethoxybenzaldehyde were dissolved in 20 ml. methanol. 67 ml. of a 14.5% solution of aqueous sodium hydroxide were added and the mixture was vigorously shaken, with cooling under running tap water to prevent the temperature rising significantly above ambient temperature. The resultant clear solution was then left to stand at ambient temperature.

After 20 minutes, the reaction mixture had set to a jelly-like mass. A thin layer chromatogram (ethyl acetate/methanol/30% aqueous trimethylamine 7:2:2 v/v/v) run after 30 minutes showed about 60% reaction. A second thin layer chromatograph run after 1.75 hours showed the reaction to be almost complete. After a further 2 hours, the reaction mixture was thoroughly mixed with 120 ml. methanol and 50 ml. ethanol, the precipitated solid was filtered off, washed thoroughly with methanol/ethanol (1:1 v/v) and dried to constant weight in a vacuum oven at 60° C., the yield being 24.6 g. of the disodium salt of 1-(4-isoprenyloxy-2-carboxymethoxyphenyl)-3-(3-carboxyphenyl)-prop-2-en-1-one. Thin layer chromatography showed this product to be approximately 97% pure.

The product was dissolved in 50 ml. hot distilled water and ethanol added until precipitation commenced. After cooling, the solid was filtered off, washed thoroughly with ethanol and dried in a vacuum oven at 60° C. to give a yield of 19.0 g. Thin layer chromatography showed the product to contain less than 1% of impurities. The pH of a 10% solution of the product was 8.5.

A sample of the disodium salt was converted into the corresponding diacid by acidification with dilute hydrochloric acid and filtering off the solid, which was washed with water until the washings were neutral and then dried. The diacid had a melting point of 168°-169° C. and the NMR spectrum supported the expected structure.

EXAMPLE 5

1-[2-(Prop-2-enyloxy)-4-carboxymethoxyphenyl]-3-(4-carboxyphenyl)-prop-2-en-1-one (a) A mixture of 35.7 g. 4-carboethoxymethoxy-2-hydroxyacetophenone, 10.8 g. potassium hydroxide and 300 ml. analytically pure dry acetone was mechanically stirred for 30 minutes at ambient temperature. 13.2 ml. Allyl bromide were then added dropwise to the resultant mixture and stirring continued for 7 hours at ambient temperature.

A thin layer chromatogram using petroleum ether (b.p. 60°-80° C.)/diethyl ether/acetone(8:1:1 v/v/v) as elution agent indicated that the reaction had reached completion. The cooled reaction mixture was filtered and the solid washed thoroughly with acetone. The filtrate was rotary evaporated to about 40 ml. and diethyl ether was added thereto. The resultant mixture was filtered, the filtrate was again concentrated to a low volume and petroleum ether (b.p. 40°-60° C.) added thereto. The crystalline material obtained was filtered off, washed with petroleum ether (b.p. 40°-60° C.) and dried to constant weight in a vacuum desiccator to give 24.86 g. of 4-carboethoxymethoxy-2-(prop-2-enyloxy)-acetophenone. A thin layer chromatogram using petroleum ether (b.p. 60°-80° C.)/diethyl ether/acetone (8:1:1 v/v/v) as elution agent indicated that the product had a purity of greater than 99%. The product had a melting point of 55°-57° C. and the infra-red spectrum showed major bands at: $\nu_{max}=1765$ (ester), 1660 (enone), 1570 and 1605 (aromatics) and 810 (aromatic 1,4-disubstituted) $cm^{-1}$. The NMR spectrum ($CDCl_3$) confirmed the expected structure.

(b) A solution of 10.56 g. sodium hydroxide in water and 8 ml. ethanol were added to 22.24 g. 4-carboethoxymethoxy-2-(prop-2-enyloxy)-acetophenone and the resultant solution was warmed in an oil bath at 65° C. The corresponding disodium salt was precipitated out and 12 g. 4-carboxy-benzaldehyde added thereto. The resulting mixture was stirred to give a solution and then followed by immediate precipitation of the product. The resultant mixture was left to stand for 10 minutes at 65° C. The precipitated product was slurried with ethanol, filtered and washed with ethanol. A thin layer chromatogram using ethyl acetate/methanol/30% aqueous trimethylamine (7:2:4 v/v/v) as elution agent indicated that the material was of 98% purity.

This material was dissolved in a minimum volume of distilled water and acidified with dilute hydrochloric acid. The solid material obtained was filtered off, washed with water until the washings were neutral and then dried to constant weight in a vacuum oven at 100° C., the yield being 22.68 g. A thin layer chromatogram using the same elution agent as above indicated that the product was of 99% purity.

22.68 g. of the product were dissolved in 1500 ml. of hot methanol/dichloromethane (1:1 v/v), the resultant solution was concentrated to 400 ml. and then left to cool. The crystalline material obtained was filtered off, washed with methanol and dried to constant weight in a vacuum oven at 85° C. There were obtained 17.68 g. of 1-[4-carboxymethoxy-2-(prop-2-enyloxy)-phenyl]-3-(4-carboxyphenyl)-prop-2-en-1-one. A thin layer chromatogram using the same elution agent as above indicated that the product was of better than 99% purity.

(c) 18.89 g. of the diacid obtained according to (b) above were slurried in 37.8 ml. methanol and to this were added dropwise 77.4 ml. of an aqueous solution of 3.92 g. sodium hydroxide, while stirring and with occasional warming, to give a clear solution with a pH of 7.50. The resultant solution was filtered and poured, while stirring, in 774 ml. of analytically pure acetone. The resultant crystalline material was filtered off, washed with acetone and dried to constant weight in a vacuum oven at 85° C. The yield was 19.54 g. of the disodium salt of 1-[2-(prop-2-enyloxy)-4-carboxymethoxyphenyl]-3-(4-carboxyphenyl)-prop-2-en-1-one which had a melting point of >300° C. and an infrared spectrum with major bands at $\nu_{max}=1640$ (enone), 1605 (broad $CO_2Na$), 1260 (ether), 1550 and 1505 (aromatic) $cm^{-1}$. A 10% solution of this disodium salt had a pH of 6.50. An NMR of the product ($D_2O$) had major signals at $\delta=4.26$ (broad singlet (4 protons, —O—$CH_2$—$CO_2Na$ and —O—$CH_2$—CH=$CH_2$) and 5.06-7.76 (12 protons multiplet, includes 7 aromatic protons, 2 ethylenic bridge protons and 3 protons from the allyl radical) Hz.

1 g. of the above disodium salt was dissolved in the minimum volume of distilled water and acidified with dilute hydrochloric acid. The precipitate obtained was filtered off, washed with water until neutral and dried to constant weight. There was obtained 0.88 g. of the corresponding diacid; m.p. 220°-222° C. A thin layer chromatogram using the same tricomponent elution as in (b) above showed that the material had a purity of better than 99%. The infra-red spectrum had major bands at $\nu_{max}=1730$ (aliphatic COOH), 1690 (aromatic COOH), 1650 (enone) and 1610 (aromatic) $cm^{-1}$. The NMR spectrum ($D_6DMSO$) confirmed the structure.

EXAMPLE 6

1-[4-(Prop-2-enyloxy)-2-caboxymethoxyphenyl]-3-(4-carboxyphenyl)-prop-2-en-1-one (a) 80 ml. analytically pure acetone were added to a mixture of 30.4 g. 2,4-dihydroxyacetophenone, 40 g. anhydrous potassium carbonate and 19.1 ml. allyl bromide and the resultant mixture was refluxed in an oil bath at 80° C. with mechanical stirring. 5 g. anhydrous potassium carbonate were added and the mixture then refluxed for a further hour. A thin layer chromatogram using petroleum ether (b.p. 60°-80° C.)/dichloromethane/acetone (6:3:1 v/v/v) as elution agent indicated that the reaction had reached completion. The cooled reaction mixture was diluted with sufficient distilled water to dissolve the inorganic material present and then extracted twice with 200 ml. amounts of diethyl ether. The ethereal layer was washed four times with 50 ml. amounts of 4% aqueous sodium hydroxide solution. The basic layer was then acidified with 25 ml. concentrated hydrochloric acid and extracted twice with 250 ml. amounts of diethyl ether. The ethereal layer was washed with water until the washings were neutral, the dried over anhydrous sodium sulphate, filtered and charcoaled. The charcoaled solution was filtered and evaporated to dryness to give 29.74 g. of 4-prop-2-enyloxy-2-hydroxyacetophenone in the form of a red oil. A thin layer chromatogram using petroleum ether (b.p. 60°-80° C.)/dichloromethane/acetone (6:3:1 v/v/v) indicated that the product had a purity better than 99%. The infra-red spectrum had major bands at $\nu_{max}$=1630 (broad hydrogen-bonded aromatic ketone), 1570, 1500 (aromatics) and 1240 (ether) $cm^{-1}$. The NMR spectrum ($CDCl_3$) confirmed the structure.

(b) A mixture of 29 g. 4-prop-2-enyloxy-2-hydroxyacetophenone, 10.75 g. potassium hydroxide and 325 ml. dry analytically pure acetone was mechanically stirred for 30 minutes at ambient temperature. 17.3 ml. Ethyl bromoacetate were added dropwise to the above mixture and stirring continued at ambient temperature for 4 hours. A thin layer chromatogram using petroleum ether (b.p. 60°-80° C.)/dichloromethane/acetone (6:3:1 v/v/v) as elution agent indicated that the reaction was 95% complete. The reaction mixture was filtered and the solid washed thoroughly with acetone. The filtrate was treated with decolorising charcoal, filtered and concentrated to 80 ml. and then left to stand at 4° C. The resultant crystalline material was filtered off, washed with acetone/water (1:1 v/v) and dried to constant weight in a vacuum desiccator. There were obtained 25.54 g. 4-prop-2-enyloxy-2-carboethoxymethoxy-acetophenone. A thin layer chromatogram using the same elution agent as above showed that the product had a better than 99% purity.

The mother liquors were left to stand at 4° C. and the crystals obtained were filtered off, washed with acetone/water (1:1 v/v) and dried to constant weight. A second crop of 4.80 g. was thus obtained, which was also better than 99% pure.

The product had a melting point of 91°-92° C. and the infra-red spectrum showed major bands at $\nu_{max}$=1750 (ester), 1655 (aromatic ketone), 1600, 1570, 1500 (aromatics) and 1265 (ether) $cm^{-1}$. The NMR spectrum confirmed the expected structure.

(c) A mixture of 13.90 g. 4-prop-2-enyloxy-2-carboethoxymethoxy-acetophenone, 50 ml. of 17% aqueous sodium hydroxide solution and 5 ml. ethanol was magnetically stirred in an oil bath at 65° C. 7.50 g. 4-Carboxybenzaldehyde were gradually added to the resultant solution and the mixture then left to stand for 10 minutes. The crystalline material obtained was slurried with ethanol, filtered, washed with ethanol and dried to constant weight in a vacuum oven at 80° C. A thin layer chromatogram using ethyl acetate/methanol/30% aqueous trimethylamine solution (7:2:4 v/v/v) indicated that the product was of better than 99% purity. The yield was 13.23 g.

This material was dissolved in 50 ml. hot water, the solution obtained having a pH of 9. The pH of the solution was adjusted to 7 with glacial acetic acid. The solution was filtered, 50 ml. of methanol were added thereto and the mixture then poured into 200 ml. ethanol, with vigorous stirring, at ambient temperature. The precipitated material was filtered off, washed with ethanol and dried to constant weight in a vacuum oven, the yield being 10.65 g. A quantitative thin layer chromatogram of a 1% solution, using the same elution agent as above, indicated that the material was of 99% purity. The product had a melting point of >300° C. and the infra-red spectrum had major bands at $\nu_{max}$=1605 (broad $CO_2Na$), 1550, 1505 (aromatic), 1265 (ether) $cm^{-1}$. A 10% aqueous solution of the product had a pH of 6.0.

1 g. of the product was acidified and the resulting diacid was washed with water until neutral and dried to constant weight in a vacuum oven at 100° C. The yield was 0.94 g. A thin layer chromatogram using the same elution agent as above indicated that the product was of 99% purity. The diacid had a melting point of 245°-247° C. and the infra-red spectrum showed major bands at $\nu_{max}$=1710 ($CO_2H$), 1650 (enone), 1610 (aromatics), 1250 (ether) $cm^{-1}$. The NMR spectrum ($d_6$-DMSO) had major signals at $\delta$=4.58 (2 proton doublet, J=8 cps, —O—$\underline{CH_2}$—CH=$CH_2$), 4.85 (2 proton singlet, —O—$\underline{CH_2}$—COOH), 5.32 (2 proton multiplet, $\underline{CH_2}$=CH—$CH_2$O—), 6.00 (1 proton multiplet, $CH_2$=CH—$CH_2$O—), 6.5-8.5 (broad 2 proton carboxylic acid protons), 7.4-8.2 (9 proton multiplet, 7 aromatic and 2 ethylenic protons) Hz.

The product thus obtained was the disodium salt of 1-[4-(prop-2-enyloxy)-2-carboxymethoxyphenyl]-3-(4-carboxyphenyl)-prop-2-en-1-one.

EXAMPLE 7

1-[4-(Prop-2-enyloxy)-2-carboxymethoxyphenyl]-3-(3-carboxyphenyl)-prop-2-en-1-one A mixture of 10.30 g. 4-prop-2-enyloxy-2-carboethoxymethoxyacetophenone, 6.07 g. 3-carbomethoxybenzaldehyde and 29.7 ml. ethanol was warmed in a waterbath. A cooled solution of 4.82 g. of sodium hydroxide in 7.40 ml. water was added thereto and shaken, while cooling. Instant precipitation of the product took place and this was left to stand for 20 minutes at ambient temperature in the absence of light. The precipitate was slurried with methanol/ethanol (1:1 v/v), filtered, washed well with methanol-ethanol(1:1 v/v) and dried to constant weight in a vacuum oven at 80° C. The yield was 10.24 g. A quantitative thin layer chromatogram of a 1% solution using ethyl acetate/methanol/30% aqueous trimethylamine solution (7:2:4 v/v/v) as elution agent indicated that the product has a purity of 98%.

This material was dissolved in a minimum volume of water and acidified with dilute hydrochloric acid. The precipitate was filtered off, washed with water until neutral and dried to constant weight in a vacuum oven at 100° C. The yield of the diacid was 8.13 g.

The diacid was dissolved in 500 ml. hot ethyl acetate/methanol (2:1 v/v), filtered and concentrated unit crystallisation was seen to commence. The crystalline material was filtered off, washed with ethyl acetate and dried to constant weight in a vacuum oven. The yield was 6.81 g. and a thin layer chromatogram, using the above elution agent, indicated that the material had a plurality of better than 99%. The product had a melting point of 220°-222° C. and the infra-red spectrum had major bands of $\nu_{max}$=1710 (aromatic $CO_2H$), 1740 (aliphatic), 1635 (enone), 1605 (aromatic), 1250 (ether) $cm^{-1}$.

The NMR spectrum ($d_6$-DMSO) had major signals at $\delta$=4.66 (2 proton doublet, J=6 cps, —O—$\underline{CH_2}$—CH=$CH_2$), 4.90 (2 proton singlet, —O—$\underline{CH_2}$COOH), 5.35 (2 proton multiplet, —O—$CH_2$=$CH_2$), 6.00 (1 proton multiplet, —O—$CH_2$—CH=$CH_2$), 4.5-6.5 (2 proton singlet broad, 2 carboxylic acid protons), 6.6-8.2 (9 proton multiplet, 7 aromatic and 2 ethylenic protons) Hz.

6.30 g. of the above diacid were slurried with 12.60 ml. methanol and a solution of 1.30 g. sodium hydroxide in 25.80 ml. water added dropwise thereto. with occasional warming to give a solution with a pH of 7.0. This solution was filtered and poured, while stirring vigorously, into 300 ml. analytically pure acetone at ambient temperature. The precipitated solid was filtered off, well washed with acetone and dried to constant weight in a vacuum oven at 80° C. The yield was 6.24 g. A thin layer chromatogram, using the above-mentioned elution agent, indicated the material to be of better than 99% purity. The disodium salt thus obtained had a melting point of >300° C. and the infra-red spectrum had major bands at 1645 (sh., enone), 1605 (broad, $CO_2Na$), 1500 (aromatic) and 1255 (ether $cm^{-1}$. A 10% aqueous solution had a pH of 6.50. The NMR spectrum ($D_2O$) confirmed the structure of the disodium salt of 1-[4-(prop-2-enyloxy)-2-carboxymethoxyphenyl]-3-(3-carboxyphenyl)-prop-2-en-1-one.

EXAMPLE 8

1-[4-(Prop-2-ynyloxy)-2-carboxymethoxyphenyl]-3-(4-carboxyphenyl)-prop-2-en-1-one (a) A mixture of 26 g. (27 ml) propargyl alcohol and 150 ml. dry pyridine was stirred in an ice/salt bath at −8° C. under anhydrous conditions. 82 g. p-toluenesulphonyl chloride were then slowly added thereto over the course of 3 hours, keeping the temperature of the reaction below −5° C. When the addition was complete, stirring at −8° C. was continued for 1 hour. A thin layer chromatogram using petroleum ether (b.p. 60°-80° C.)/dichloromethane/acetone (6:3:1 v/v/v) as elution agent indicated that the reaction was 80% complete. The reaction mixtures was poured into 600 ml. ice/concentrated hydrochloric acid and extracted twice with 250 ml. amount of diethyl ether. The ethereal solution was washed twice with a saturated aqueous solution of sodium bicarbonate and then with distilled water until the washings were neutral. The ethereal layer was dried with anhydrous sodium sulphate, filtered and rotary evaporated to dryness. There were obrtained 33.35 g. of the tosylate of propargyl alcohol. A thin layer chromatogram using the above elution agent indicated that the material was of 98% purity.

(b) 26.7 ml. of analytically pure dry acetone were added to a mixture of 12.94 g. 4-hydroxy-2-carboethoxymethoxyacetophenone, 7.60 g. anhydrous potassium carbonate and 11.41 g. of the tosylate of propargyl alcohol, whereafter the reaction mixture was refluxed for 2 hours in an oil bath at 80° C., while stirring mechanically. A thin layer chromatogram using petroleum ether (b.p. 60°-80° C.)/dichloromethane/acetone (6:3:2 v/v/v) as elution agent showed that the reaction was 40% complete. A further 1 g. anhydrous potassium carbonate and 15 ml. analytically pure dry acetone were added and the resultant mixture refluxed for 2 hours, whereafter a thin layer chromatogram using the above elution agent showed that the reaction was 85% complete. The reaction mixture was diluted with acetone, filtered and the solid obtained thoroughly washed with acetone. The filtrate was concentrated to a low volume on a rotary evaporator and left to stand at 4° C. The crystalline material obtained was filtered off and washed with acetone. A thin layer chromatogram using the above elution agent indicated that the material was of 98% purity. This material was dissolved in 150 ml. of hot methanol/dichloromethane (2:1 v/v), concentrated to a low volume and left to stand at 4° C. The crystalline material obtained was filtered off, washed with a small amount of methanol and dried in a vacuum oven at 60° C. There were obtained 8.14 g of 4-(prop-2-ynyloxy)-2-carboethoxymethoxyacetophenone; m.p. 133°-135° C. A thin layer chromatogram using the above elution agent indicated the material to be of better than 99% purity.

(c) 8 g. 4-Prop-2-ynyloxy)-2-carboethyoxymethoxyacetophenone were added to 29 ml. of a 17% aqueous sodium hydroxide solution and 2.90 ml. ethanol. The resultant mixture was stirred in an oil bath at 65° C. and 4.34 g. 4-carboxybenzaldehyde were gradually added thereto over the course of 10 minutes, whereafter the reaction mixture was further stirred for 15 minutes. A thin layer chromatogram using ethyl acetate/methanol/30% aqueous trimethylamine solution (7:2:4 v/v/v) indicated that the reaction was virtually complete. The reaction mixture was diluted with 29 ml. methanol and then poured, with vigorous stirring, in 400 ml. ethanol at ambient temperature. The precipitated material was filtered off, washed with methanol/ethanol(1:1 v/v), dissolved in distilled water and acidified with dilute hydrochloric acid. The precipitated material was filtered off, washed with water until neutral and dried to constant weight in a vacuum oven at 100° C. to give 7.39 g. of 1-[4-(prop-2-ynyloxy)-2-carboxymethoxyphenyl]-3-carboxyphenyl)-prop-2-en-1-one. A thin layer chromatogram using the above elution agent indicated the product was of 95% purity.

7.39 g. of this product were dissolved in 40 ml. dimethylformamide in an oil bath at 120° C., while stirring, and distilled water added until just cloudy, whereafter it was left to cool. The crystalline material was filtered off, washed with dimethylformamide/water (1:1 v/v) and dried to constant weight in a vacuum oven at 80° C. to give a yield of 2.58 g. Working up the mother liquors gave a second crop of 1.61 g. A thin layer chromatogram using the above elution agent indicated that both crops were of 97% purity. The two crops were combined and recrystallised to give 1.95 g. of a first crop and 1.33 of a second crop, a thin layer chromatogram using the above elution agent indicating that both crops were of 98% purity.

These two crops were combined and refluxed for 1 hour in 100 ml. ethyl acetate/methanol (1:1 v/v). The resultant suspension was filtered and the solid obtained was washed with ethyl acetate and then dried to constant weight, the yield being 3.05 g. A thin layer chromatogram using the above elution agent indicated that the material was of 99% purity.

EXAMPLE 9

1-[4-(Hex-5-enyloxy)-2-carboxymethoxyphenyl]-3-(4-carboxyphenyl)-prop-2-en-1-one (a) A mixture of 50 g. 2,4-dihydroxyacetophenone, 68.1 g. anhydrous potassium carbonate and 500 ml. analytically pure acetone was prepared and 56.3 g. (39.4 ml.) benzyl bromide added thereto, whereafter the mixture obtained was heated for 4 hours in an oil bath at 50° C., with mechanical stirring, whereafter a thin layer chromatogram using petroleum ether (b.p. 60°-80° C.)/dichloromethane/acetone (6:3:1 v/v/v) as elution agent indicated the reaction to be 85% complete. The cooled reaction mixture was filtered and the insoluble matter thoroughly washed with acetone. The filtrate was charcoaled, filtered and the filtrate rotary evaporated to dryness to give 92.56 g. 4-benzyloxy-2-hydroxyacetophenone.

This material was dissolved in hot ethanol, concentrated to a low volume and then left to cool. The crystalline material obtained was filtered off, washed with ethanol and dried to constant weight in a vacuum oven at 80° C., the yield being 61.08 g. A thin layer chromatogram using the above elution agent indicated the material to be of better than 99% purity; m.p. 103°-104° C.

(b) 28.6 ml. Ethyl bromoacetate were added to a mixture of 60 g. 4-benzyloxy-2-hydroxyacetophenone and 17.14 g. potassium hydroxide in 857 ml. dry, analytically pure acetone. The resultant mixture was mechanically stirred at ambient temperature for 8 hours, whereafter a thin layer chromatogram using petroleum ether (b.p. 60°-80° C.)/dichloromethane/acetone (6:3:1 v/v/v) as elution agent indicated the reaction to be complete. The reaction mixture was filtered and the insoluble material thoroughly washed with acetone. The filtrate was rotary evaporated to dryness to give 103.21 g. 4-benzyloxy-2-carboethoxymethoxyacetophenone.

This material was dissolved in 350 ml. hot ethanol, concentrated to a low volume and then left to cool. The crystalline material obtained was filtered off, washed with ethanol and dried to constant weight in a vacuum oven at 80° C., the yield being 73.22 g. A thin layer chromatogram using the above elution agent indicated that the material was of better than 99% purity; m.p. 123°-124° C.

(c) 1.16 g. of 5% palladium-on-charcoal catalyst was added to a suspension of 58 g. 4-benzyloxy-2-carboethoxymethoxyacetophenone in 580 ml. ethyl acetate and the resultant mixture was hydrogenated while shaking and heating, the total uptake of hydrogen after 4 hours being 4065 ml. The reaction mixture was filtered through a pad of "Hyflo-cell" and the filtrate concentrated to 100 ml. The crystalline material obtained was filtered off, washed with a small amount of ethyl acetate and dried to constant weight in a vacuum oven at 80° C. to give 32.50 g. 4-hydroxy-2-carboethoxymethoxyacetophenone, a thin layer chromatogram using petroleum ether (b.p. 60°-80° C.)/dichloromethane/acetone (6:3:2 v/v/v) indicating the material to be of 98% purity.

Recrystallisation of this material from 150 ml. ethyl acetate gave a yield of 26.83 g., a thin layer chromatogram using the above elution agent indicating the material to be of better than 99% purity; m.p. 122°-123° C. The mother liquors were worked up to give a second crop of 4.30 g. of better than 99% purity.

(d) 10 ml. dry acetone were added to a mixture of 5.95 g. 4-hydroxy-2-carboethoxymethoxyacetophenone, 3.50 g. anhydrous potassium carbonate and 4.075 g. (3.35 ml.) 6-bromohex-1-ene. The resultant mixture was refluxed in an oil bath at 80° C. for 6 hours, with mechanical stirring, a further 1 g. of anhydrous potassium carbonate being added after 2 hours. A thin layer chromatogram using the same elution agent as in (c) above indicated that the reaction was 30% complete. A further 1 ml. 6-bromohex-1-ene, 1 g. anhydrous potassium carbonate and 5 ml. dry acetone were added to the reaction mixture, followed by refluxing for a further 6 hours. A thin layer chromatogram using the same elution agent as above then indicated the reaction to be 70% complete. A further 1 ml. 6-bromohex-1-ene and 1 g. anhydrous potassium carbonate were added and refluxing continued for 7 hours, whereafter a thin layer chromatogram with the same elution agent as above indicated that the reaction had reached completion.

The reaction mixture was then diluted with sufficient distilled water to dissolve inorganic materials and then extracted twice with 50 ml. amounts of diethyl ether. The ethereal layer was washed with a saturated aqueous solution of sodium bicarbonate and then with water until the washings were neutral. The ethereal layer was then dried with anhydrous sodium sulphate, filtered and the filtrate rotary evaporated to dryness, the yield of 4-(hex-5-enyloxy)-2-carboethoxymethoxyacetophenone being 8.11 g. A thin layer chromatogram using the same elution agent as above indicated that the material was of 99% purity.

1 g. of this material was dissolved in 15 ml. distilled petroleum ether (b.p. 60°-80° C.) at ambient temperature and left to stand. The crystalline material obtained was filtered off, washed with a little petroleum ether (b.p. 60°-80° C.) and dried to constant weight in a vacuum desiccator, the yield being 0.05 g. A thin layer chromatogram using the same elution agent as above indicated that the material was of better than 99% purity; m.p. 47°-48° C.

(e) A mixture of 10 ml. of 17% aqueous sodium hydroxide solution and 1 ml. ethanol was added to 3.20 g. 4-(hex-5-enyloxy)-2-carboethoxymethoxyacetophenone and the resultant solution was magnetically stirred in an oil bath at 65° C., 1.50 g. 4-carboxybenzaldehyde being gradually added thereto over a period of 10 minutes, followed by stirring for a further 15 minutes. A thin layer chromatogram using ethyl acetate/methanol/30% aqueous trimethylamine solution (7:2:4 v/v/v) as elution agent indicated that the reaction was virtually complete. The reaction mixture was diluted with 10 ml. methanol and poured in 100 ml. ethanol, while stirring at ambient temperature. The precipitated solid was filtered off, washed with methanol/ethanol (1:1 v/v) and dried to constant weight in a vacuum oven to give (2.41 g. of 1-[4-hex-5-enyloxy)-2-carboxymethoxyphenyl]-3-(4-carboxyphenyl)-prop-2-en-1-one.

This product was dissolved in a minimum volume of distilled water and acidified with dilute hydrochloric acid. The precipitated solid was filtered off, washed with water until neutral and dried to constant weight in a vacuum oven at 100° C., the yield being 1.92 g.

This diacid was suspended in 30 ml. hot ethyl acetate and sufficient methanol added to give a clear solution which was concentrated to 20 ml. and then left to cool. The crystalline material obtained was filtered off, washed with ethyl acetate and dried to constant weight in a vacuum oven at 80° C., the yield being 1.06 g. A thin layer chromatogram using the same elution agent as above indicated that the material was of 98% purity. It was again crystallised from ethyl acetate to give a yield of 0.87 g., a thin layer chromatogram using the same elution agent as above indicating a plurality of better than 99%. The product had a melting point of 229°-231° C.

EXAMPLE 10

1-[4-But-3-enyloxy)-2-carboxymethoxyphenyl]-3-(4-carboxyphenyl)-prop-2-en-1-one (a) 13 ml. dry, analytically pure acetone were added to a mixture of 7.74 g. 4-hydroxy-2-carboethoxymethoxyacetophenone, 4.55 g. anhydrous potassium carbonate and 4.39 g. (3.33 ml.) 4-bromobut-1-ene and the mixture obtained refluxed for 8 hours in an oil bath at 80° C., with mechanical stirring, 1 g. of anhydrous potassium carbonate being added every 2 hours. A thin layer chromatogram using petroleum ether (b.p. 60°-80° C.)/dichloromethane/acetone (6:3:2 v/v/v) as elution agent indicated that the reaction was 40% complete. A further 1 g. 4-bromobut-1-ene, 1 g. anhydrous potassium carbonate and 5 ml. dry, analytically acetone were added thereto, followed by refluxing for 4 hours, whereafter a thin layer chromatogram using the same elution agent as above indicated that no further reaction had taken place. A further 1 g. 4-bromobut-1-ene and 1 g. anhydrous potassium carbonate were added, followed by refluxing for 6 hours, whereafter a thin layer chromatogram indicated that the reaction was 60% complete.

The reaction mixture was diluted with sufficient distilled water to dissolve the inorganic materials present and then extracted twice with 100 ml. amounts of diethyl ether. The ethereal layer was washed with a saturated aqueous solution of sodium bicarbonate and then with water until neutral. The ethereal layer was dried over anhydrous sodium sulphate, filtered and rotary evaporated to dryness to give 7.15 g. of impure 4-(but-3-enyloxy)-2-carboethoxymethoxyacetophenone. A thin layer chromatogram using the same elution agent as above indicated that the material only contained 60% of the desired product.

A large column was packed with 200 g. of silica gel. 5.51 g. of the above impure product were preadsorbed into 20 g. of silica gel, poured on to the top of the column and the topped up with sand. The column was eluted with petroleum ether (b.p. 60°-80° C.)/diethyl ether (70:30 v/v) and 100 ml. fractions were collected. The pure product was collected in 10 fractions which were combined and rotary evaporated to dryness, the yield being 3.14 g. A thin layer chromatogram using the above elution agent indicated that the product was of over 99% purity; m.p. 50°-51° C.

(b) 2.94 g. 4-(but-3-enyloxy)-2-carboxyethoxymethoxyacetophenone were added to a mixture of 10 ml. of 17% aqueous sodium hydroxide solution and 1 ml. ethanol. The resultant solution was magnetically stirred in an oil bath at 65° C. and 1.50 g. 4-carboxybenzaldehyde gradually added thereto over a period of 10 minutes, followed by further stirring for 15 minutes at 65° C. A thin layer chromatogram using ethyl acetate/methanol/30% aqueous trimethylamine solution (7:2:4 v/v/v) as elution agent indicated that the reaction was virtually complete. The reaction mixture was diluted with 10 ml. of methanol and poured, with vigorous stirring, into 100 ml. ethanol at ambient temperature. The precipitated material was filtered off and washed with methanol/ethanol (1:1 v/v).

This material was dissolved in a minimum volume of distilled water and acidified with dilute hydrochloric acid. The precipitate obtained was filtered off, washed with water until the washings were neutral and dried to constant weight in a vacuum oven at 100° C. there being obtained 2.01 g. of 1-[4-(but-3-enyloxy)-2-carboxymethoxyphenyl)-3-(4-carboxyphenyl)-prop-2-en-1-one. A thin layer chromatogram using the above elution agent indicated that the product was of 98% purity.

This material was dissolved in 75 ml. hot ethyl acetate/methanol (2:1 v/v) and concentrated to 20 ml. The crystalline material obtained was filtered off, washed with ethyl acetate and dried to constant weight in a vacuum oven at 80° C., the yield being 1.23 g. A thin layer chromatogram using the same elution agent as above indicated that the material was of better than 99% purity; m.p. 237°-238° C.

The following examples illustrate pharmaceutical compositions containing the new chalcone derivatives of the present invention, these compositions being suitable for administration to humans for the treatment of ulcerative conditions of the gastrointestinal tract:

EXAMPLE A

| | |
|---|---|
| disodium salt of 1-(4-isoprenyloxy-2-carboxymethoxyphenyl)-3-(4-carboxyphenyl)-prop-2-en-1-one | 50 mg. |
| lactose, extra fine | 145 mg. |
| microcrystalline cellulose | 96 mg. |
| croscarmellose sodium | 6 mg. |
| magnesium stearate | 3 mg. |
| | 300 mg. |

EXAMPLE B

| | |
|---|---|
| disodium salt of 1-(4-carboxymethoxy-4-isoprenyloxyphenyl)-3-(4-carboxymethoxyphenyl)-prop-2-en-1-one | 100 mg. |
| lactose, extra fine | 219 mg. |
| microcrystalline cellulose | 146 mg. |
| croscarmellose sodium | 25 mg. |
| magnesium stearate | 10 mg. |
| | 500 mg. |

EXAMPLE C

| | |
|---|---|
| disodium salt of 1-[2-(prop-2-enyloxy)-4-carboxymethoxyphenyl]-3-(4-carboxyphenyl)-prop-2-en-1-one | 100 mg. |
| lactose | 280 mg. |
| starch | 100 mg. |
| alginic acid | 10 mg. |
| magnesium stearate | 10 mg. |
| | 500 mg. |

We claim:

1. A chalcone derivative of the general formulae:

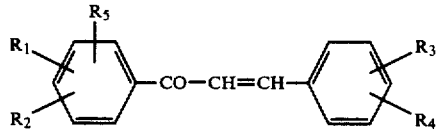

(IIa)

wherein $R_1$ is a carboxyalkyoxy radical, $R_2$ is an unsaturated, straight-chained or branched aliphatic hydrocarbonyloxy radical, $R_3$ is a hydrogen atom, a hydroxyl group or an alkoxy radical, $R_4$ is a carboxyalkoxy or carboxyalkylcarbonyloxyalkyl radical or a carboxylic acid group and $R_5$ is a hydrogen or halogen atom *with the proviso that when $R_4$ is a carboxymethoxy radical $R_3$ is other than a hydrogen atom*; and the nontoxic inorganic and organic salts of those compounds containing at least one carboxylic acid [or sulphonic acid] group.

2. A chalcone derivative according to claim 1, wherein the carboxyalkoxy radicals $R_1$ and $R_4$ have the general formulae $$-O\text{-}(CH_2)_n COOH$$

in which n is 1, 2 or 3.

3. A chalcone derivative according to claim 1, which is 1-(4-isoprenyloxy-2-carboxymethoxyphenyl)-3-(4-carboxyphenyl)-prop-2-en-1-one and the disodium salt thereof.

[4. A chalcone derivative according to claim 1, which is 1-(2-Carboxymethoxy-4-isoprenyloxyphenyl)-3-(4-carboxymethoxyphenyl)-prop-2-en-1-one and the disodium salt thereof.]

5. A chalcone derivative according to claim 1, which is 1-(2-Carboxymethoxy-4-isoprenyloxyphenyl)-3-(4-carboxymethoxy-3-methoxyphenyl)-prop-2-en-1-one and the disodium salt thereof.

6. A chalcone derivative according to claim 1, which is 1-(4-Isoprenyloxy-2-carboxymethoxyphenyl)-3-(3-carboxyphenyl)-prop-2-en-1-one and the disodium salt thereof.

7. A chalcone derivative according to claim 1, which is 1-[2-(Prop-2-enyloxy)-4-carboxymethoxyphenyl]-3-(4-carboxyphenyl)-prop-2-en-1-one and the disodium salt thereof.

8. A chalcone derivative according to claim 1, which is 1-[4-(Prop-2-enyloxy)-2-carboxymethoxyphenyl]-3-(4-carboxyphenyl)-prop-2-en-1-one and the disodium salt thereof.

9. A chalcone derivative according to claim 1, which is 1-[4-(Prop-2-enyloxy)-2-carboxymethoxyphenyl]-3-(3-carboxyphenyl)-prop-2-en-1-one and the disodium salt thereof.

10. A chalcone derivative according to claim 1, which is 1-[4-(Prop-2-ynyloxy)-2-carboxymethoxyphenyl]-3-(4-carboxyphenyl)-prop-2-en-1-one.

11. A chalcone derivative according to claim 1, which is 1-[4-(Hex-2-enyloxy)-2-carboxymethoxyphenyl]-3-(4-carboxyphenyl)-prop-2-en-1-one.

12. A chalcone derivative according to claim 1, which is 1-[4-(But-2-enyloxy)-2-carboxymethoxyphenyl]-3-(4-carboxyphenyl)-prop-2-en-1-one.

13. Pharmaceutical compositions containing at least one chalcone derivative according to claim 1, in admixture with a solid or liquid pharmaceutical diluent or carrier.

* * * * *